United States Patent
Klemetti

(10) Patent No.: US 7,418,237 B2
(45) Date of Patent: Aug. 26, 2008

(54) ELECTRIC CIRCUIT AND TRANSMISSION METHOD FOR TELEMETRIC TRANSMISSION

(75) Inventor: Janne Klemetti, Oulunsalo (FI)

(73) Assignee: Polar Electro Oy, Kempele (FI)

( * ) Notice: Subject to any disclaimer, the term of this patent is extended or adjusted under 35 U.S.C. 154(b) by 530 days.

(21) Appl. No.: 11/010,647

(22) Filed: Dec. 13, 2004

(65) Prior Publication Data

US 2005/0135039 A1    Jun. 23, 2005

(30) Foreign Application Priority Data

Dec. 16, 2003  (FI) .................................. 20031840

(51) Int. Cl.
  *H04B 5/00* (2006.01)
(52) U.S. Cl. ............... 455/41.1; 455/336; 455/334; 455/337; 455/343.1; 455/317; 455/423; 607/32
(58) Field of Classification Search ............ 455/336, 455/334, 337, 343.1, 338, 318, 317, 423; 607/32
See application file for complete search history.

(56) References Cited

U.S. PATENT DOCUMENTS

| | | | |
|---|---|---|---|
| 3,513,311 A | 5/1970 | McAlister et al. | |
| 3,746,999 A * | 7/1973 | Freen | 455/334 |
| 4,625,733 A | 12/1986 | Säynäjäkangas | |
| 5,287,113 A | 2/1994 | Meier | |
| 5,630,216 A * | 5/1997 | McEwan | 455/215 |
| 6,072,371 A * | 6/2000 | Kobayashi et al. | 331/49 |
| 6,421,535 B1 * | 7/2002 | Dickerson et al. | 455/338 |
| 6,658,300 B2 * | 12/2003 | Govari et al. | 607/60 |
| 6,873,838 B2 * | 3/2005 | Mapes | 455/336 |
| 7,046,122 B1 * | 5/2006 | Forster | 340/10.33 |

FOREIGN PATENT DOCUMENTS

| | | |
|---|---|---|
| DE | 1204731 | 9/1970 |
| EP | 0747003 | 12/1996 |
| EP | 0831416 | 3/1998 |
| WO | WO 91/16696 | 10/1991 |

* cited by examiner

*Primary Examiner*—Lana N. Le
*Assistant Examiner*—Ping Y Hsieh
(74) *Attorney, Agent, or Firm*—Hoffmann & Baron, LLP

(57) ABSTRACT

The invention relates to an electric circuit for a telemetric transmission. A semiconductor transistor switch switches a quenching circuit into an electrically conductive state to prevent oscillation of a resonance circuit. The semiconductor transistor switch switches the quenching circuit into a state preventing the passage of electric current to enable oscillation of the resonance circuit. The quenching circuit comprises at least one restriction component for preventing the passage of a base current of the semiconductor transistor switch when the semiconductor transistor switch is switched open.

14 Claims, 5 Drawing Sheets

ELECTRIC CIRCUIT AND TRANSMISSION METHOD FOR TELEMETRIC TRANSMISSION

CROSS-REFERENCE TO RELATED APPLICATION

This application claims priority based on Finnish Patent Application No. 20031840, filed on Dec. 16, 2003 which is incorporated herein by reference.

FIELD OF THE INVENTION

An electric circuit and a transmission method for a telemetric transmission.

BRIEF DESCRIPTION OF THE RELATED ART

Vital functions can be measured telemetrically by the use of a non-invasive measuring device. An example of such a measuring device is a system for measuring the heart rate, the system comprising a plurality of functional units, such as a transmitter unit, a receiver unit and a data transfer unit. Each functional unit usually comprises a battery acting as the power source for the unit. A transmitter unit refers to a transmitter unit held against a human body, particularly the chest, and is provided with electrodes, and often implemented in the shape of a transmitter belt attachable around the body. A receiver unit refers to a watch-like receiver unit held for instance on the wrist and being in telemetric interaction based on inductive activity with the transmitter unit. The data transfer unit, which is in a telemetric connection with the receiver unit, can be used to transfer data accumulated in the receiver unit to a computer, for example. A computer can also be used to control both the transmitter and receiver units via the data transfer unit;

Transmitters of heart rate measuring devices, for example, may transmit an about 5-kHz inductive burst every time they detect an ECG signal. The transmitter circuit of the transmitter unit may be a resonance circuit composed of a capacitor and a coil, for example, which is controlled to oscillate by bursts at each heart beat. These bursts are typically detected at the receiver with an antenna and a receiving structure corresponding to the transmitter. Instead of or in addition to the heart rate, the data telemetrically transferred may generally consist of a plurality of measurement data of different measurement variables, such as working frequency, pedalling speed, pedalling frequency, propagation speed, etc.

The resonance circuit continues to oscillate unless its oscillation is actively cancelled. A semiconductor transistor switch is usually coupled between the poles of the resonance circuit, the switch being opened for the duration of the transmission of each burst. The switch is closed after each burst, whereby the energy of the oscillator circuit is discharged rapidly and the oscillator circuit does not transmit interference oscillations during the time between the bursts. At the same time, the length of the burst can be set as desired.

However, problems are associated with this solution. The quenching circuit loads the oscillation circuit also during resonance oscillation, since the semiconductor transistor switch leaks current although it is switched to the open state. For this reason, the resonance circuit has to be controlled by a higher power than the need would be without the quenching circuit, which is shown as increased power consumption and a faster running down of the accumulator or the piles.

SUMMARY OF THE INVENTION

The object of the invention is to implement an improved electric circuit.

This object is achieved with an electric circuit for an inductively implemented low-frequency telemetric transmission, the electric circuit comprising a direct current source for supplying electric power to the electric circuit; a resonance circuit for telemetric transmission; a quenching circuit coupled to the resonance circuit and comprising a semiconductor transistor switch; the semiconductor transistor switch being configured to switch the quenching circuit into an electrically conductive state to prevent oscillation of the resonance circuit, and the semiconductor transistor switch being configured to switch the quenching circuit into a state preventing the passage of electric current to enable oscillation of the resonance circuit. The quenching circuit further comprises at least one electric restriction component for preventing the passage of a base current of the semiconductor transistor switch when the semiconductor transistor switch is switched open.

The invention also relates to a telemetric, inductive and low-frequency transmission method comprising switching a quenching circuit, coupled with a semiconductor transistor switch to a resonance circuit, into an electrically conductive state to prevent oscillation of the resonance circuit; and switching the quenching circuit with the semiconductor transistor switch into a state preventing the passage of electric current to enable oscillation of the resonance circuit. The method further comprises preventing the passage of electric current on a base of the semiconductor transistor switch when the semiconductor transistor switch is switched open with at least one electric restriction component comprised by the quenching circuit.

Preferred embodiments of the invention are described in the dependent claims.

The method and system of the invention bring forth a plurality of advantages. The driving power of the resonance circuit can be kept low, since the leakage of electric current taking place in the quenching circuit is eliminated. This way power consumption remains low, and accumulators and batteries last longer.

BRIEF DESCRIPTION OF THE DRAWINGS

In the following, the invention will be described in more detail in connection with preferred embodiments with reference to the accompanying drawing, in which.

DETAILED DESCRIPTION OF THE PREFERRED EMBODIMENTS

The solution presented is suitable for use for instance in connection with a heart rate monitor, a speedometer and a cadence meter, without, however, being restricted to them.

Figure 1:
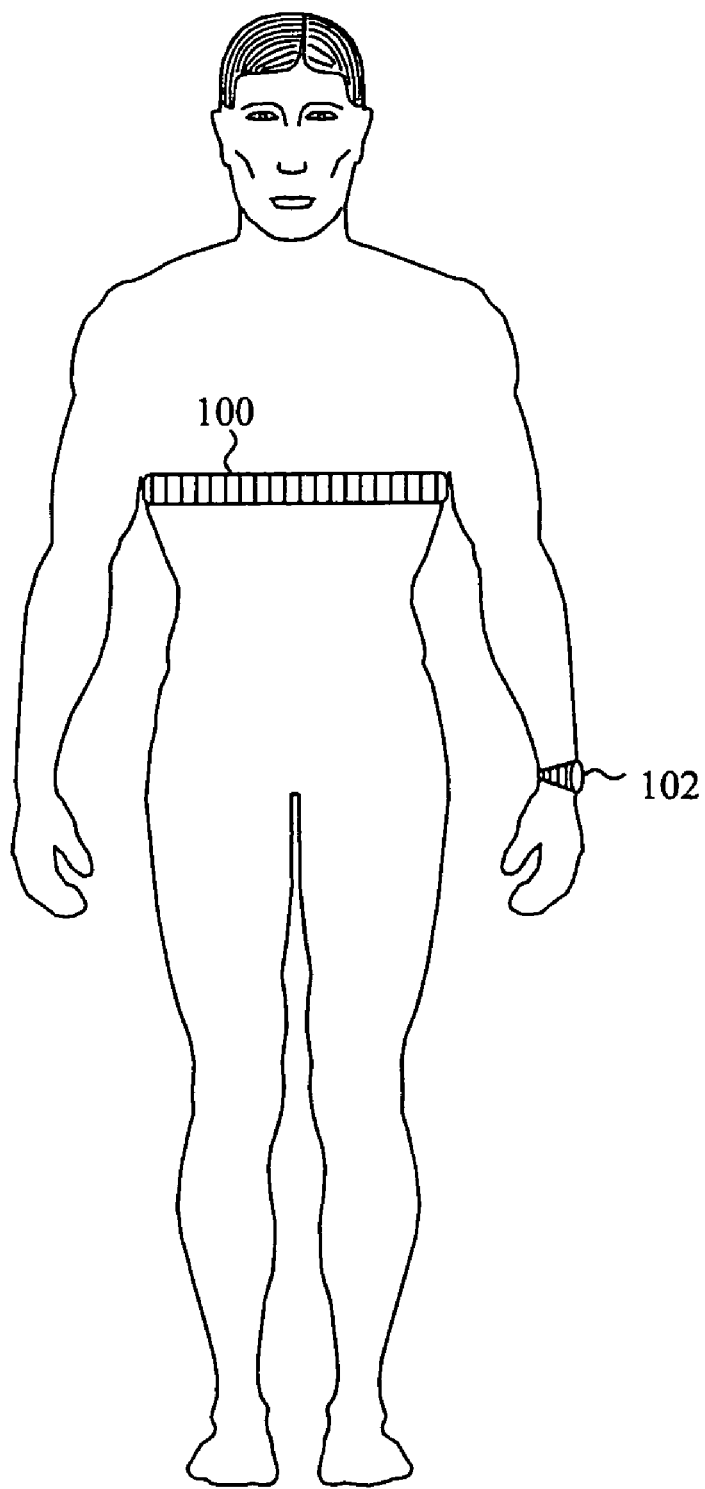
FIG. 1 shows a heart rate monitor.

Let us now study the solution presented by means of FIG. 1. A heart rate monitor may comprise a transmitter unit 100 for measuring the heart rate and attached around the chest. In addition, the user may have on his wrist a heart rate monitor receiver unit 102, to which the transmitter unit 100 may transmit data. The electric circuit presented may be employed in a telemetric data transfer system, wherein data is transferred at a distance from the body to a limb.

Figure 2:
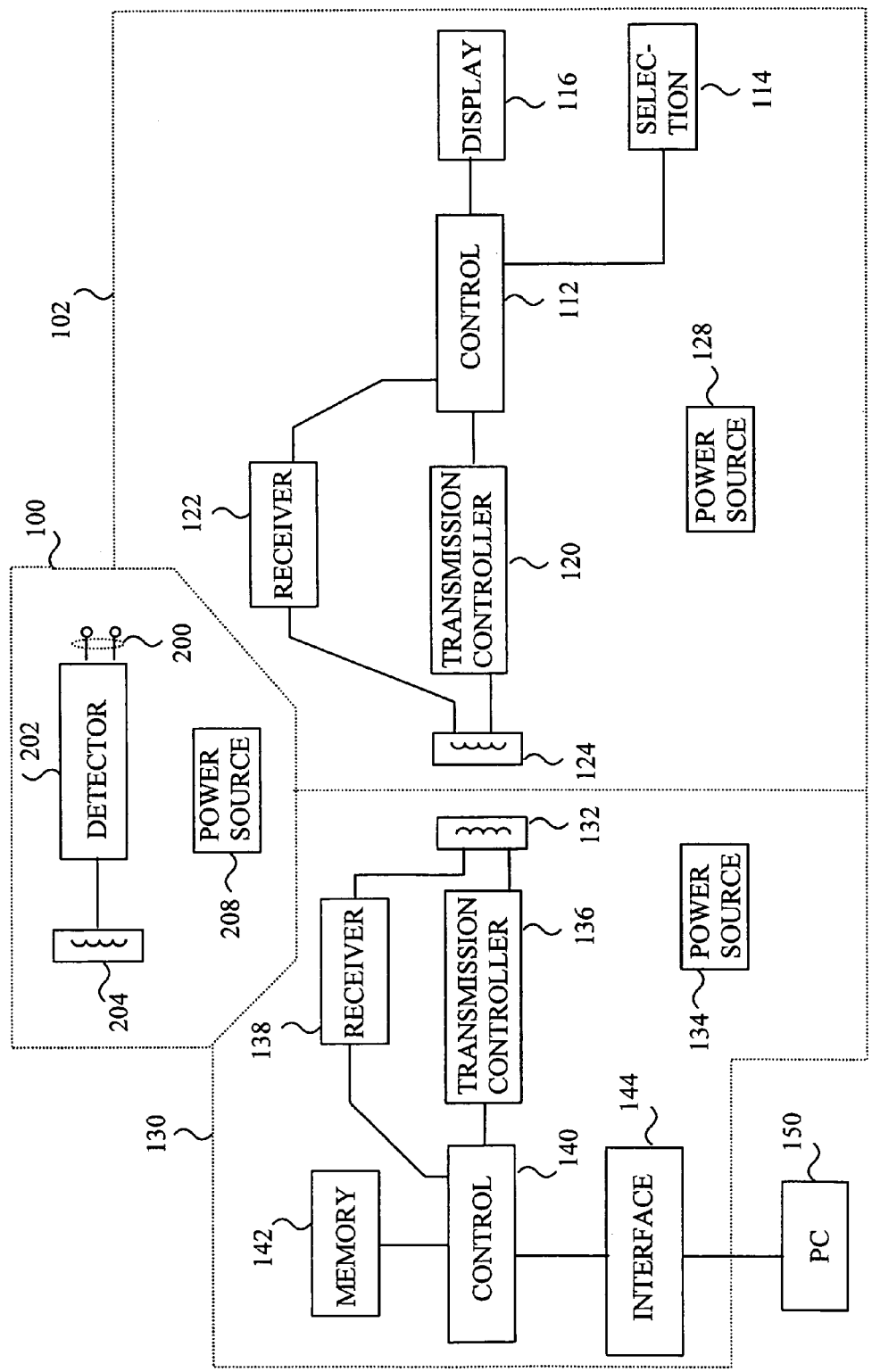
FIG. 2 shows a block diagram of a heart rate monitor.

Let us now study an electronic device associated with heart rate measurement in more detail by means of FIG. 2. This device is an example of many alternatives whereto the solution presented can be applied. As main parts of the heart rate monitor, the arrangement may comprise a telemetric transmitter unit 100 and a telemetric receiver unit 102. In addition, the heart rate monitor may comprise a data transfer unit 130 for transferring data to a data processing and control unit 150, which may be a PC, for example.

The transmitter unit 100 may comprise ECG electrodes 200, an ECG pre-amplification and pulse detection block 202 with filters, a resonance circuit 204 and a power source 208. The block 202 controls the resonance circuit 204 by a signal corresponding to the heart rate. Since data transfer is based on the use of a magnetic field, the resonance circuit 204 generates a magnetic field that varies in sync with the heart rate and that the resonance circuit 204 can use for inductive interaction with for instance a resonance circuit 124 of the receiver unit 102, and thus the transmission unit 100 is able to transfer the measured heart rate to the receiver unit 102. The power source 208 generates the electric power required by all blocks of the transmitter unit 100 (for the sake of clarity, FIG. 3 does not show power supply conductors). The power source 208 may be chargeable.

The transmitter unit 100 may also comprise a memory (not shown in FIG. 2), whereby the transmitter unit 100 does not necessarily require a receiver unit 102 as its pair, but the transmitter unit 100 is able to store its measurement data in the memory, from where the measurement data can be unloaded for instance via the data transfer unit 130 to a computer 150 for processing and perusal.

The receiver unit 102 may comprise a controlling control part 112. The control part 112 may also control a user interface, which may comprise selection means 114 and display means 116. The selection means 114 are typically a keyboard, with which the user uses the receiver unit 102. The display means 116, such as an LCD screen, provide a user with visual information. The control part 112 typically comprises a microprocessor and memory. The control part 112 may be implemented with an ASIC circuit or other electronics components. The receiver 102 further comprises a transmission controller 120, receiver means 122 and a resonance circuit 124. The transmission controller 120 may transfer data from the receiver unit 102 to the data transfer unit 130 inductively by using the resonance circuits 124 and 132. The receiver means 122 may use the resonance circuit 124 also for receiving data inductively and convert it into digital for the microprocessor 112. The receiver unit 102 also comprises a power source 128.

Typically, the receiver unit 102, kept on the wrist in the same way as a wristwatch, may also independently measure the heart rate with sensors (not shown in FIG. 2). The measurement may take place optically and/or with a pressure sensor, for example. In this case, the receiver unit 102 substantially comprises the functions of both a receiver 102 and a transmitter 100 and, consequently, a separate transmitter unit 100 is not necessarily a part of the measurement system.

The data transfer unit 130 may comprise a resonance circuit 132, a transmission controller 136, a receiver 138, a processing unit, such as a microprocessor 140, a memory 142, an interface 144, and a power source 134. Via the interface 144, the data transfer unit 130 communicates with the data processing unit 150, e.g. a PC. The resonance circuit 132 of the data transfer unit 130 is tuned to the same resonance frequency as the resonance circuit 124 of the receiver unit 102. The function of the transmission controller 136 is to control the resonance circuit 132. The function of the receiver 138 is to receive series-form data coming from the resonance circuit 124 via the resonance circuit 132. The data transfer may also be implemented by using other data transfer manners, known per se, such as an acoustic signal, an infrared signal or an RF signal. The microprocessor 140 converts the data transfer into a form suitable for the PC (the data processing unit 150). When required, the memory 142 of the data transfer unit 130 may store the files read. The interface 144, which may be RS232, for example, converts the voltage levels of the interface into suitable for the interface employed. The power source 134 may supply electric power to all the blocks of the data transfer unit 130.

The power source 208, 128 or 134 of the transmitter unit 100, the receiver unit 102 or the data transfer unit may be a battery, accumulator, chargeable accumulator or the like, which produces direct current. The resonance circuits 124, 132 and 204, in turn, are tuned according to the data transfer frequency employed for the resonance.

Figure 3:
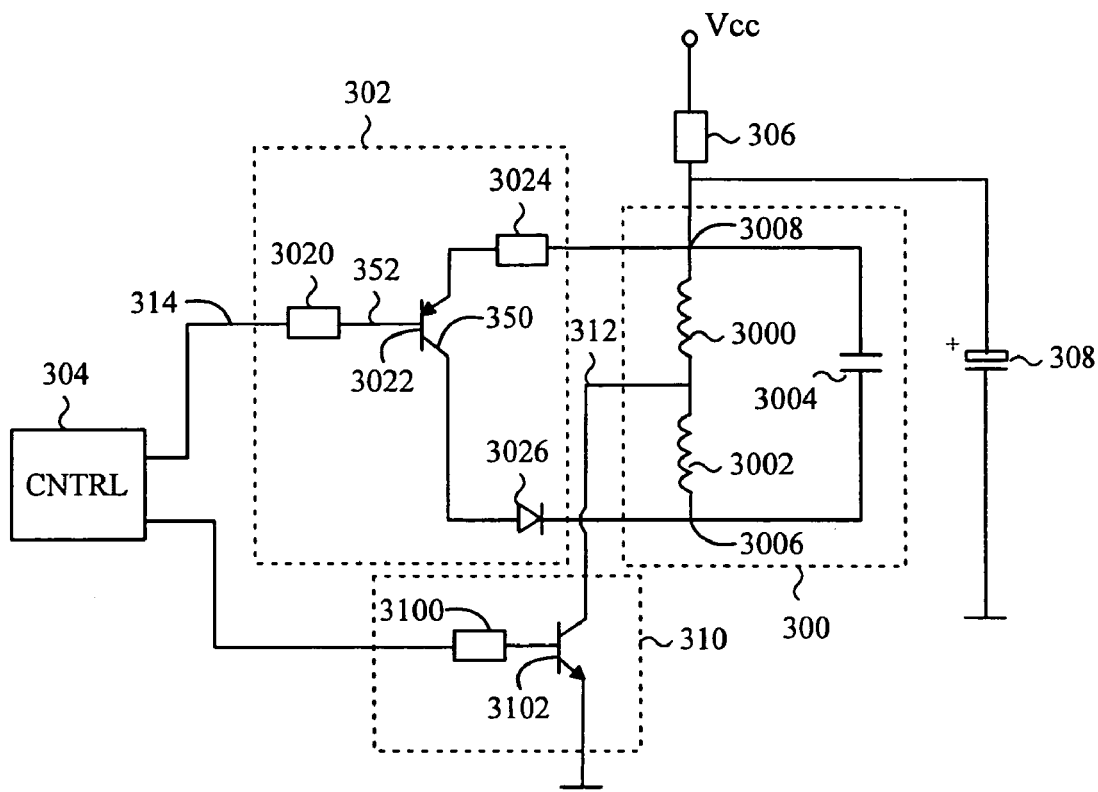
FIG. 3 shows a restriction component leading from a collector to a pole of an oscillation circuit.

Let us now study an embodiment of the solution presented by means of FIG. 3. The solution comprises a resonance circuit 300, which corresponds to the resonance circuits 124, 132 and 204 of FIG. 2, a quenching circuit 302 and a controller 304. As is the case in FIG. 3, the resonance circuit 300 may comprise two coils 3000, 3002 in series and a capacitor 3004 in parallel with the coils, but the implementation may be different, too. The quenching circuit 302 may comprise a semiconductor transistor switch 3022, to whose base is coupled a resistor 3020 acting on the control current, a current restrictor resistor 3024 and an electric restriction component 3026, which prevents the passage of electric current in the quenching circuit 302 at least against the direction defined by the direct current source. In this way, the passage of the base current of the semiconductor transistor switch 3022 is prevented, i.e. in this case, the passage of electric current is prevented from the collector 350 of the semiconductor transistor switch 3022 to the base 352 when the semiconductor transistor switch 3022 is switched open, whereby the quenching circuit is in a state that does not attenuate the oscillation of the resonance circuit. In the solution presented, taken more generally, base current refers to the electric current arriving at the base 352 of the semiconductor transistor switch 3022, the current propagating from the base 352 to the inside of the semiconductor transistor switch 3022 or from the inside of the semiconductor transistor switch 3022 to the base 352, acting on the state of the semiconductor transistor switch 3022. The semiconductor transistor switch 3022 may be a PNP transistor, such as is shown in FIG. 3. Generally, the transistor acting as the semiconductor transistor switch 3022 may be a BJT (Bipolar Junction Transistor) or of the FET type (Field Effect Transistor). In FIG. 3, the electric restriction component 3026 is a diode.

The quenching circuit 302 may comprise more than one restriction component. The semiconductor transistor switch 3022 switches the quenching circuit 302 into an attenuating state to prevent oscillation of the resonance circuit 300. This being so, the quenching circuit 302 is electrically conductive, and the difference in potential between the poles 3006 and 3008 of the resonance circuit 300 remains unchanged. The difference in potential is usually very small in relation to the voltage of the direct current source Vcc, or nonexistent. Similarly, the semiconductor transistor switch 3022 switches the quenching circuit 302 into a non-attenuating state to enable oscillation of the resonance circuit 300. This being so, the quenching circuit 302 is not electrically conductive or at least the electrical conductivity is lower than in the attenuating state, whereby a varying difference in potential may be generated between the poles 3006 and 3008 of the resonance circuit 300. A current-restricting resistor 306 may be provided between the positive pole of the direct current source Vcc and the resonance circuit 300. The voltage of the direct current source Vcc may be a few volts. In addition, an optionally employed capacitor 308 decreases variations in the electrical current supplied by the power source Vcc.

Feeding a bursty control signal 312 from a final amplifier circuit 310, which may comprise a base resistor 3100 and a transistor 3102, makes the resonance circuit 300 oscillate at its resonance frequency. The oscillation of the resonance circuit is low-frequency oscillation, wherein low frequency refers to an oscillation below 200 kHz. The transistor 3102 may be an NPN transistor, a darlington transistor or a darlington coupling. The controller 304 controls the feed of the control signal. The control signal 312 may be fed in between the coils 3000 and 3002. This way the coils 3000 and 3002 constitute a varying magnetic field according to the resonance frequency of the circuit, the field being telemetrically detectable.

During the oscillation of the resonance circuit 300, the potential of the pole 3006 may temporarily rise higher than the potential of the pole 3008. When the controller 304 controls the resonance circuit 300 to oscillate, the controller 304 controls the semiconductor transistor switch 3022 to switch on, whereby no current is supposed to pass in the quenching circuit 302. However, without the electric restriction component 3026, the semiconductor transistor switch 3022 leaks electric current through the semiconductor transistor switch 3022 particularly when the potential of the pole 3006 of the resonance circuit 300 is higher than the potential of the pole 3008 of the resonance circuit 300. This being so, the direction of the electric current is temporarily from the pole 3006 to the pole 3008. The leakage current decreases the amplitude of the oscillation and the power of the telemetric transmission, the resonance circuit 300 being subjected to stronger control for rectifying this. Increasing the control power, in turn, shortens the operating time of the battery employed as the direct current source.

When employing the electric restriction component 3026 for preventing the passage of the base current of the semiconductor transistor switch 3022 when the semiconductor transistor switch 3022 is switched open, the problem caused by the leakage current of the semiconductor transistor switch 3022 is eliminated, since electric current is unable to propagate, even during a major difference in potential, through the diode from the collector 350 to the base 352 of the semiconductor transistor switch 3022. In this embodiment, the passage of electric current is thus prevented in the quenching circuit from the pole 3006 to the pole 3008 when the semiconductor transistor switch 3022 is switched open. This is possible when a diode that conducts electricity in the direction from the pole 3008 to the pole 3006 is employed as the electric restriction component 3026. In this case, the cathode of the diode can be coupled to the pole 3006, and the anode of the diode can be coupled to the collector 350 of the semiconductor transistor switch, as is shown in FIG. 3.

Figure 4:
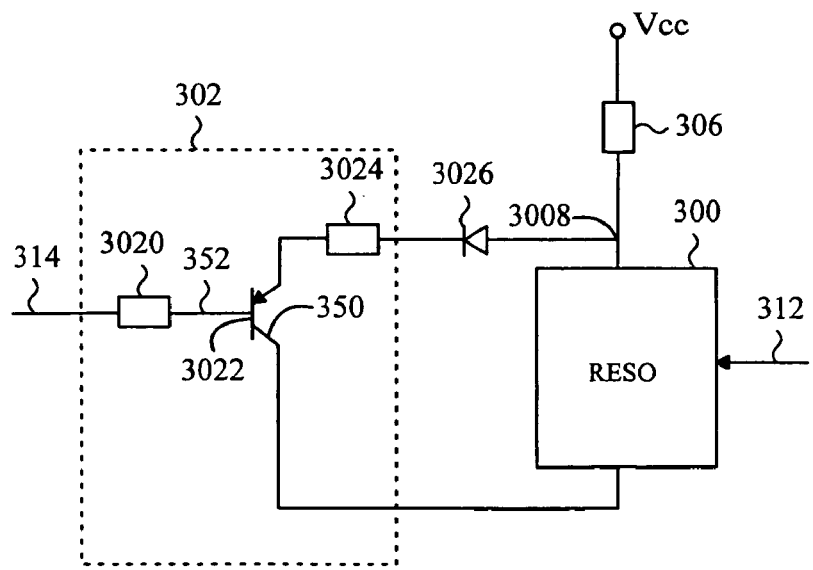
FIG. 4 shows a restriction component leading from the pole of a resonator to an emitter.

The diode employed as the electric restriction component 3026 in FIG. 4 is placed in between the semiconductor transistor switch 3022 and the pole 3008. This being so, the cathode of the diode can be coupled to the pole of the resistor 3024 and the anode of the diode can be coupled to the pole 3008. However, conducting in the same direction, the diode can be located on either side of the optional resistor 3024, whereby the diode is placed in the portion of the quenching circuit 302 between the semiconductor transistor switch 3022 and the positive pole of the direct current source Vcc.

Figure 5:
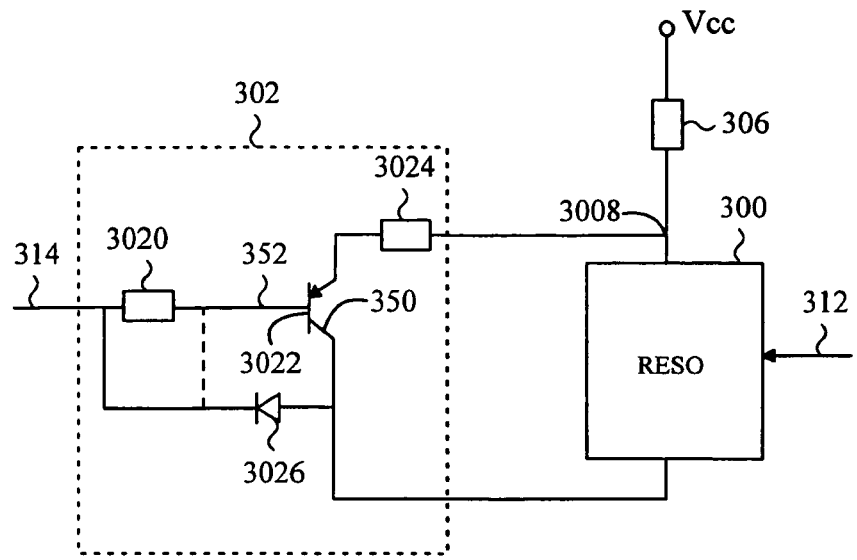
FIG. 5 shows a restriction component leading from a collector to a pole of a base resistor.

The diode employed as the electric restriction component 3026 in FIG. 5 may be placed in parallel with the collector 350 and the pole 352 of the semiconductor transistor switch 3022 (the broken line is associated with this coupling). Alternatively, the diode may also be placed in parallel with the base resistor 3020 over the collector 350 and the pole 352 of the semiconductor transistor switch 3022 (this coupling is drawn in its entirety with a solid line). This being so, the feedforward direction of the diode is from the collector 350 to either pole of the base resistor 3020. When the diode is in parallel with the collector base interface and the base resistor 3020, the base resistor 3020 separates the cathode of the diode from the base 352 of the semiconductor transistor switch 3022, the anode being coupled to the collector 350 of the semiconductor transistor switch 3022. During oscillation, as the potential of the collector tends to rise, depending on the coupling of the resistor 3020, the diode keeps the potential of either pole and the collector 350 (nearly) the same (the diode at a threshold voltage that is below 1V), thus preventing the passage of the base current acting on the state of the semiconductor transistor switch 3022. Because of this, no electric current leaks through the switched-open semiconductor transistor switch 3022, which enables disturbance-free operation of the resonance circuit 300.

As the diode, any semiconductor component can be employed whose conductivity as a function of the voltage between the poles corresponds to a conventional diode, i.e. electric current passes well only in one direction. Consequently, as the diode, for instance an NPN transistor can be employed, whose base and collector are coupled together as an anode, the emitter operating as the cathode of the diode coupling.

Figure 6:
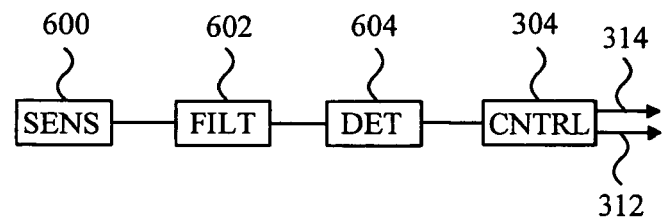
FIG. 6 shows the generation of signals controlling a resonance circuit and a quenching circuit.

FIG. 6 shows a block diagram of a circuit solution for generating the signals controlling the resonance circuit and the quenching circuit. At least one sensor 600 can be employed to measure the desired object. The object may be the heart, a vehicle, a fitness device etc. and the measurement data may be the heart rate, the speed of the vehicle, the working frequency etc. The measuring signal can be filtered in the desired manner with filters 602, and the desired measurement data can be indicated from the filtered signal with an indicator 604. The measurement data may be the heart rate frequency, the variation in the heart rate frequency, the cadence etc. A controller 606, which may comprise a controller 304 and a transistor stage 310, controls the quenching circuit and the oscillation circuit according to the measurement data with signals 312 and 314.

The speed sensor associated with the solution presented may be implemented for instance with a magnetic switch sensor such that a magnet is fastened to a wheel of a bicycle or the like, and the switch part of the sensor is in position for instance in the frame structure (front fork) of the device, the speed measurement being based on detection of the movement of the magnet past the switch part of the sensor. Correspondingly, a cadence transmitter is intended for measuring the pedalling frequency (or another performance frequency of a movement) of a pedaller. A cadence sensor may be implemented for instance with a magnetic switch sensor such that the magnet is fastened to the pedal of a bicycle and the switch part of the sensor and the actual transmitter unit are fastened in position for instance to the frame tube of the bicycle, the measurement of the cadence, i.e. the pedalling frequency, being based on detection of the movement of the magnet past the switch part of the sensor.

Figure 7:
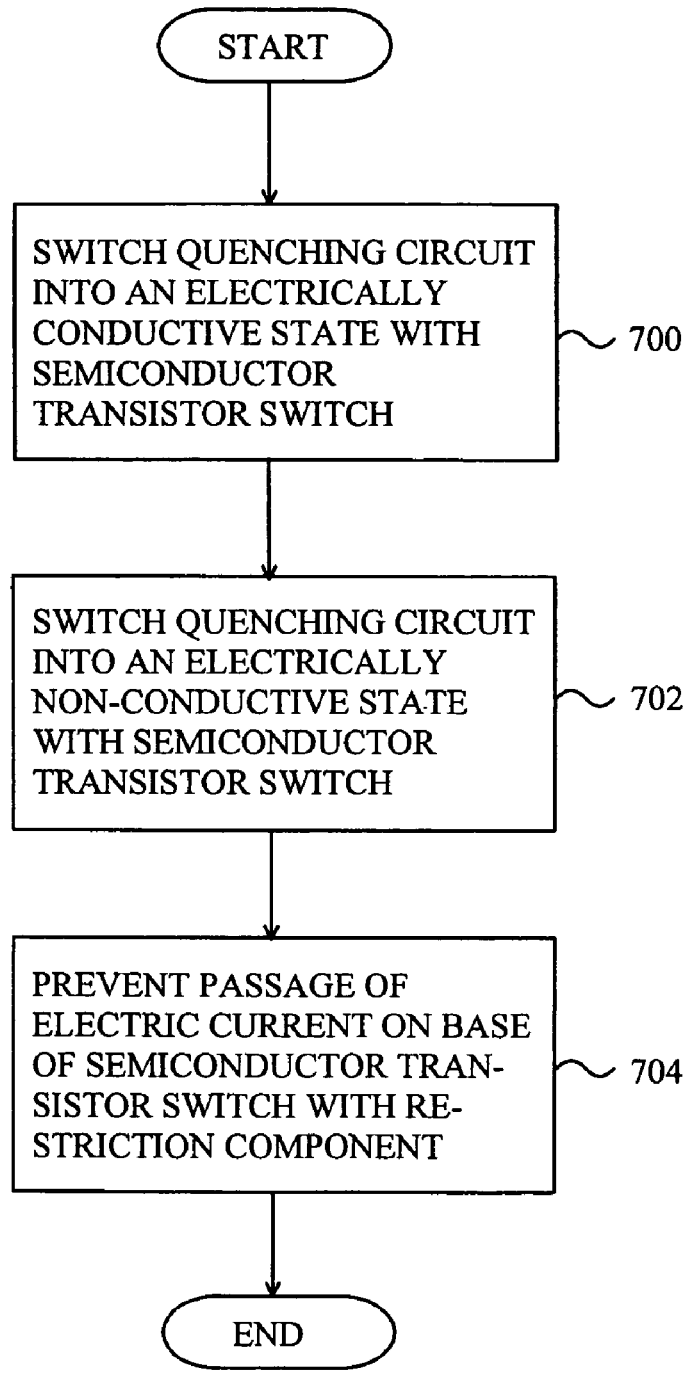
FIG. 7 shows a flow diagram according to the method.

FIG. 7 shows a flow diagram according to the method. In step 700, the quenching circuit 302, coupled to the resonance circuit 300 with the semiconductor transistor switch 3022, is switched into an electrically conductive state to prevent oscillation of the resonance circuit 300. In step 702, the quenching circuit 302 is coupled with the semiconductor transistor switch 3022 into a state preventing the passage of electric current to enable oscillation of the resonance circuit 300. In step 704, the at least one electric restriction component 3026 comprised by the quenching circuit 302 is used to prevent the passage of electric current on the base of the semiconductor transistor switch 3022 when the semiconductor transistor switch 3022 is switched open.

Although the invention is described herein with reference to the example in accordance with the accompanying drawings, it will be appreciated that the invention is not to be so limited, but it may be modified in a variety of ways within the scope of the appended claims.

What is claimed is:

1. An electric circuit for an inductively implemented low-frequency telemetric transmission, the electric circuit comprising:
    a direct current source for supplying electric power to the electric circuit;
    a resonance circuit for telemetric transmission; and
    a quenching circuit coupled to the resonance circuit and comprising a semiconductor transistor switch, the semiconductor transistor switch being configured to switch the quenching circuit into an electrically conductive state to prevent oscillation of the resonance circuit, and the semiconductor transistor switch being configured to switch the quenching circuit into a state preventing the passage of electric current to enable oscillation of the resonance circuit, wherein the quenching circuit comprises at least one electric restriction component for preventing the passage of a base current of the semiconductor transistor switch when the semiconductor transistor switch is switched open, wherein at least one electric restriction component comprised by the quenching circuit is a diode coupled between one pole of the resonance circuit and the semiconductor transistor switch in a non-conducting direction to prevent the passage of current from a collector to a base of the semiconductor transistor switch.

2. An electric circuit as claimed in claim 1, wherein at least one electric restriction component comprised by the quenching circuit is a diode coupled in a forward direction in parallel with a collector and a base of the semiconductor transistor switch.

3. An electric circuit as claimed in claim 1, wherein at least one electric restriction component comprised by the quenching circuit is a diode coupled in parallel with a collector of the semiconductor transistor switch and a base resistor in a forward direction from the collector to a pole of the base resistor.

4. An electric circuit as claimed in claim 1, wherein at least one electric restriction component is placed in the quenching circuit on a stretch from the semiconductor transistor switch and to a pole of the resonance circuit, the pole being farther from a positive pole of the direct current source when propagating from the positive pole of the direct current source towards a negative pole of the direct current source.

5. An electric circuit as claimed in claim 1, wherein at least one electric restriction component is placed in a portion of the quenching circuit between the semiconductor transistor switch and a positive pole of the direct current source.

6. An electric circuit as claimed in claim 1, wherein the electric circuit telemetrically transfers data between a body and a limb.

7. A telemetric, inductive and low-frequency transmission method comprising:
    switching a quenching circuit, coupled with a semiconductor transistor switch to a resonance circuit, into an electrically conductive state to prevent oscillation of the resonance circuit;
    switching the quenching circuit with the semiconductor transistor switch into a state preventing the passage of electric current to enable oscillation of the resonance circuit;
    preventing the passage of electric current on a base of the semiconductor transistor switch when the semiconductor transistor switch is switched open with at least one electric restriction component comprised by the quenching circuit; and
    preventing the passage of electric current from a collector to the base of the semiconductor transistor switch with at least one electric restriction component comprised by the quenching circuit comprises a diode coupled between one pole of the resonance circuit and the semiconductor transistor switch in a non-conducting direction.

8. An electric circuit for an inductively implemented low-frequency telemetric transmission, the electric circuit comprising:
    a direct current source for supplying electric power to the electric circuit;
    a resonance circuit for telemetric transmission; and
        a quenching circuit coupled to the resonance circuit and comprising a semiconductor transistor switch, the semiconductor transistor switch being configured to switch the quenching circuit into an electrically conductive state to prevent oscillation of the resonance circuit, and the semiconductor transistor switch being configured to switch the quenching circuit into a state preventing the passage of electric current to enable oscillation of the resonance circuit, wherein the quenching circuit comprises at least one electric restriction component for preventing the passage of a base current of the semiconductor transistor switch when the semiconductor transistor switch is switched open, wherein at least one electric restriction component is placed in the quenching circuit on a stretch from the semiconductor transistor switch and to a pole of the resonance circuit, the pole being farther from a positive pole of the direct current source when propagating from the positive pole of the direct current source towards a negative pole of the direct current source.

9. An electric circuit as claimed in claim 8, wherein at least one electric restriction component comprised by the quenching circuit is a diode coupled between one pole of the resonance circuit and the semiconductor transistor switch in a non-conducting direction to prevent the passage of current from a collector to a base of the semiconductor transistor switch.

10. An electric circuit as claimed in claim 8, wherein at least one electric restriction component comprised by the quenching circuit is a diode coupled in a forward direction in parallel with a collector and a base of the semiconductor transistor switch.

11. An electric circuit as claimed in claim 8, wherein at least one electric restriction component comprised by the quenching circuit is a diode coupled in parallel with a collector of the semiconductor transistor switch and a base resistor in a forward direction from the collector to a pole of the base resistor.

12. An electric circuit as claimed in claim 8, wherein at least one electric restriction component is placed in a portion of the quenching circuit between the semiconductor transistor switch and a positive pole of the direct current source.

13. An electric circuit as claimed in claim 8, wherein the electric circuit telemetrically transfers data between a body and a limb.

14. A telemetric, inductive and low-frequency transmission method comprising:

switching a quenching circuit, coupled with a semiconductor transistor switch to a resonance circuit, into an electrically conductive state to prevent oscillation of the resonance circuit;

switching the quenching circuit with the semiconductor transistor switch into a state preventing the passage of electric current to enable oscillation of the resonance circuit;

preventing the passage of electric current on a base of the semiconductor transistor switch when the semiconductor transistor switch is switched open with at least one electric restriction component comprised by the quenching circuit; and placing at least one electric restriction component in the quenching circuit on a stretch from the semiconductor transistor switch and to a pole of the resonance circuit, the pole being farther from a positive pole of the direct current source when propagating from the positive pole of the direct current source towards a negative pole of the direct current source.

* * * * *